(12) United States Patent
Herruzo Cabrera (10) Patent No.: US 6,908,628 B2
(45) Date of Patent: Jun. 21, 2005

(54) DISINFECTANT AND ANTISEPTIC COMPOSITION

(75) Inventor: Rafael Herruzo Cabrera, Madrid (ES)

(73) Assignee: OFTRAI, S.L., Madrid (ES)

( * ) Notice: Subject to any disclaimer, the term of this patent is extended or adjusted under 35 U.S.C. 154(b) by 0 days.

(21) Appl. No.: 10/166,017

(22) Filed: Jun. 10, 2002

(65) Prior Publication Data

US 2003/0099717 A1 May 29, 2003

(30) Foreign Application Priority Data

Jun. 15, 2001 (ES) .......................................... 200101398

(51) Int. Cl.$^7$ ........................ A01N 33/12; A01N 37/04; A01N 59/00; A01N 59/16; A01N 47/44; A61K 33/40; A61K 33/38; A61K 31/19; A61K 31/155; A61P 2/18

(52) U.S. Cl. ........................ 424/616; 424/600; 424/617; 424/618; 424/619; 424/661; 424/662; 424/663; 424/664; 424/665; 424/666; 424/667; 424/668; 424/669; 424/670; 424/671; 424/672; 424/677; 424/678; 424/679; 424/680; 424/681; 424/682; 424/723; 424/78.08; 424/78.09; 424/78.37; 424/94.1; 424/94.2; 424/94.6; 424/94.61; 424/94.63; 424/94.64; 514/492; 514/495; 514/557; 514/574; 514/634; 514/635; 514/642; 514/643; 514/772; 514/772.1; 422/28; 422/37

(58) Field of Search ................................ 424/616–619, 424/600, 661–672, 677–682, 723, 78.08, 78.09, 78.37, 94.1, 94.2, 94.6, 94.61, 94.63, 94.64; 514/492, 495, 557, 574, 634, 635, 642, 643, 772, 772.1; 422/28, 37, 29

(56) References Cited

U.S. PATENT DOCUMENTS

| | | | |
|---|---|---|---|
| 2,917,428 A | | 12/1959 | Hitzman |
| 3,297,456 A | | 1/1967 | Newell |
| 4,900,721 A | | 2/1990 | Bansemir et al. |
| 4,942,041 A | * | 7/1990 | Guhl et al. ................. 424/613 |
| 5,578,134 A | * | 11/1996 | Lentsch et al. ................. 134/3 |
| 5,779,914 A | * | 7/1998 | Brown et al. ................. 210/754 |
| 6,448,062 B1 | * | 9/2002 | Huth et al. ................. 435/264 |
| 6,627,657 B1 | * | 9/2003 | Hilgren et al. .............. 514/553 |

FOREIGN PATENT DOCUMENTS

| | | | |
|---|---|---|---|
| EP | 0 185 970 | | 7/1986 |
| EP | 0 252 278 | | 1/1988 |
| EP | 0 423 922 | | 4/1991 |
| EP | 1 027 827 | | 8/2000 |
| GB | 2 076 286 | | 12/1981 |
| JP | 59 164400 | | 9/1984 |
| JP | 06 192692 | | 7/1994 |
| WO | 94/00548 | * | 1/1994 |

OTHER PUBLICATIONS

Chemical Abstracts 119:103423 (1993).*
Herruzo Cabrera, R. "Spanish disinfectants for the 21$^{st}$ century." *Anales de La eal Academia Nacional De Medicina*, vol. 117, No. 4 (2000) pp 791–812.
English Abstract of JP 06 192692 dated Jul. 12, 1994.
English Abstract of EP 0 185 970 dated Jul. 2, 1986.
English Abstract of JP 59 164400 dated Sept. 17, 1984.

* cited by examiner

*Primary Examiner*—John Pak
(74) *Attorney, Agent, or Firm*—Ladas & Parry LLP (57) ABSTRACT

Wide spectrum disinfecting and antiseptic composition for use in the fields of human medicine, veterinary science and industry, characterized because it includes:

Hydrogen peroxide, lactic acid and halogen salts (Br, I) and/or salts of heavy metals (for example, silver halides) with surfactant agents, either cationic, like chlorhexidine and/or quaternary ammonium salts, like didecyl-methyl-polyoxy-ethyl-ammonium propionate, chlorides of ammonium or compounds of ammonium propylamide or anionic, like lauryl sulphate, dodecyl sulphate or alkyl succinic salts, with suitable excipients, some of which may be ethyl or isopropyl alcohol, chlorhexidine, non-chlorinated quaternary ammonium salts, like didecyl-methyl-polyoxy-ethyl-ammonium propionate, combined or not with iodine, and/or its salts, together with excipients, some of which may be ethyl or isopropyl alcohol.

28 Claims, 2 Drawing Sheets

DISINFECTANT AND ANTISEPTIC COMPOSITION

FIELD OF THE INVENTION

This invention refers to a new disinfectant and antiseptic composition.

The disinfecting component of this wide spectrum composition comprises oxidising agents, like hydrogen peroxide, lactic acid and halogen salts (Br, I) and/or heavy metals, plus surfactants, that is:

a) cationic surfactants, like quaternary ammonium and/or biguanidines, like chlorhexidine, or b) anionic surfactants, like lauryl sulphate, alkyl succinic or dodecyl sulphate salts.

All of them with the suitable excipients (alcohol, water, etc.).

The antiseptic component of the composition binds chlorhexidine to non-chlorinated quaternary ammonium like didecylmethylpolyoxyethylammonium propionate with iodine or iodinated salts and suitable excipients, like dyes, emollients and alcohol.

This disinfectant and antiseptic composition may be used in the field of medicine, veterinary science or industry.

BACKGROUND OF THE INVENTION

Disinfecting instruments for hospital use involves a key factor for the control of hospital infections. There are several methods and products used to perform said disinfecting. A review of the main methods and disinfecting products for hospital use, together with their indications and risks may be found in the tenth edition of the book by Piedrola Gil, "Medicina Preventiva y Salud Pública" (Preventive Medicine and Public Health), Ed Masson (Barcelona), in Chapter 37, pages 413–424, written by Herruzo Cabrera et al.

This chapter shows the advantages and drawbacks of 2% glutaraldehyde, the reference disinfectant and the need of finding a suitable alternative for it, since its toxicity makes it a problem for the users and even for patients, if the disinfected material is not thoroughly rinsed. An alternative may be the combination of lactic acid to hydrogen peroxide, since it combines non-toxicity to a wide microbicidal capacity. This was the object of patent PCT/ES98/00151, in whose claims includes 3–6% hydrogen peroxide, 5–15% lactic acid and combined with the previous mixture, a compound selected from 0.4–5% chlorhexidine or 0.1–3% lauryl sulphate of an alkaline metal and water as a balance, where all the percentages are with respect to the total composition. However, this compound is very acid, which may involve a problem for its use, and if its components are reduced by dilution, its disinfecting power is lost, so that it is necessary to reinforce this activity and reduce its acidity.

The present invention corrects these problems by using the similar products with ranges which are different to those claimed and adds others which are vital to considerably enhance its microbicidal effectiveness, besides providing the product with a considerable dilution capacity, cheapening it and even permitting its use as an antiseptic, in specific formulations, designed for such a purpose.

DETAILED DESCRIPTION OF THE INVENTION

This invention provides a disinfecting and antiseptic composition, comprising oxidising agents, like hydrogen peroxide, lactic acid and halogen salts (and/or heavy metal salts), together with surfactants, that is, a biguanidine like chlorhexidine with or without quaternary ammonium, or anionic surfactants, like lauryl sulphate, alkyl succinic or dodecyl sulphate salts. Additionally, the composition of the invention may contain water and some suitable excipients, like alcohol.

On the other hand, the composition is also antiseptic, based on chlorhexidine and non-chlorinated quaternary ammonium like didecyl methyl-polyoxy-ethyl-ammonium propionate, with iodine (metallic or in salts) and suitable excipients, like emollients and alcohol.

Hydrogen peroxide is an oxidising disinfectant, of medium activity against a plurality of micro-organisms. In its undiluted formulation, the disinfectant composition of the invention may contain 0.16–2.9% or 6.1–22.5% hydrogen peroxide with respect to the total.

Lactic acid, increasing the effectiveness of hydrogen peroxide may be available in an amount comprised between 0.1% and 24%.

Chlorhexidine is a biguanidine with a powerful antimicrobial activity, but has little effectiveness against virus and mycobacteria, such that in disinfecting it should be combined with other products. In the present invention, in the undiluted formula, it may be present at a concentration comprised between 5.1% and 18%.

Lauryl sulphate is an anionic surfactant with a wide detergent effect, but with reduced microbicidal power, frequently used in soaps for washing hands. This disinfectant composition may contain it in a ratio comprised between 3.1% and 20%.

It may be substituted by another anionic agent, like alkyl succinic or dodecyl sulphate, with proportions similar to the anionic surfactants, with respect to the total, although it is preferable to reduce them to 1–12%.

The quaternary ammonium salts are cationic surfactants frequently used in disinfecting and antisepsis, although problems have been described related to their use due to bacteria becoming resistant to them, but may be very useful when combined with other products, since they aid in the destruction of bacteria walls. In its undiluted formulation, these products will be in a wide ratio, from 0.2% to 50%.

The halogens, like Br and I, are also frequently used in antisepsis and disinfecting and usually act by generating oxidising by-products of the microbial components. In the composition of this invention, they are incorporated at a ratio comprised between 0.001% and 5 of the undiluted formula.

The heavy metal salts, like silver, cerium, etc., are widely used in disinfectants and antisepsis, acting by accumulation of the latter in the bacterial cytoplasm. In the composition of this invention, they were incorporated in the range from 0.00002% to 2% in undiluted formulas.

The disinfecting and antiseptic composition of the invention may also contain a balance of water and excipients, normally used in disinfectant composition formulations, for example, food preserving agents, dyes, enzymes and alcohol.

In one of the preferred embodiments of the invention, the ranges of the basic substances are as follows:

| | |
|---|---|
| hydrogen peroxide | 0.16–2.9% or 6.1–22.5% |
| lactic acid: | 0.2–20% |

-continued

| | |
|---|---|
| chlorhexidine | 5.1–18% |
| excipients and water | (balance) | where all the percentages are by weight with respect to the total.

In another of the preferred embodiments of the invention, the disinfectant composition ranges are:

| | |
|---|---|
| hydrogen peroxide: | 0.16–2.9% or 6.1–22.5% |
| lactic acid: | 0.2–20% |
| alkaline metal lauryl sulphate: | 3.1–20% |
| excipients and water | (balance) | where all the percentages are by weight with respect to the total.

Chlorhexidine or lauryl sulphate may also be replaced by quaternary ammonium salts, or by mixing chlorhexidine with the quaternary ammonium salts to give the surfactant compound which binds to the hydrogen peroxide base, lactic acid and heavy metal salts and/or halogen salts (Br, I). Alcohol may also be added to improve evaporation and the antimicrobial effectiveness. They may also bind to enzymes like trypsin, amylase and lipase to give enzymatic disinfectants.

Another example to be used in antisepsis is the following one in an undiluted formulation:

| | |
|---|---|
| chlorhexidine: | 0.2–18% |
| didecyl-methyl-polyoxy-ethyl-ammonium propionate: | 1–45% |
| iodine (metallic or its salts): | 0.01–5% |
| excipients (one of them may be ethyl or isopropyl alcohol) | |

The disinfecting and antiseptic composition of the invention is very useful as a wide spectrum disinfectant and especially destined to be used in any field, veterinary, industrial or human medicine, since it is very useful as a disinfecting agent for instruments (for example, high level disinfecting in certain semi-critical instruments, like flexible endoscopes) surfaces, conduits, etc.

For disinfecting, a suitable amount of the product of the invention should be applied, diluted according to the indication and quickness required over the material or surface to be disinfected. This application may be performed by any conventional method like immersion, spraying, injection, impregnation with the aid of a suitable applicator for the disinfecting composition over the conduits, surface or instruments to be disinfected, both in the field of human medicine and that of veterinary medicine or industry.

Some of its components are originally separated and combined at the time of use or dilution in water. At this time, the mixture is considered as activated and has a variable shelf-life, which in general exceeds two weeks (which may be increased with suitable preserving agents), although if contaminated objects are introduced, etc. it is not convenient to let the solution to age, making it recommendable to eliminate the dilutions at the end of the day.

On the other hand, the composition object of the invention may also be used as an antiseptic, both in human and veterinary medicine, it being possible to deposit it over the skin like other antiseptics, by immersion, application, spraying, etc. The antiseptic composition is already reconstituted (it is not necessary to mix its components "in situ") and has a minimum shelf-life of two years.

Figure 1:
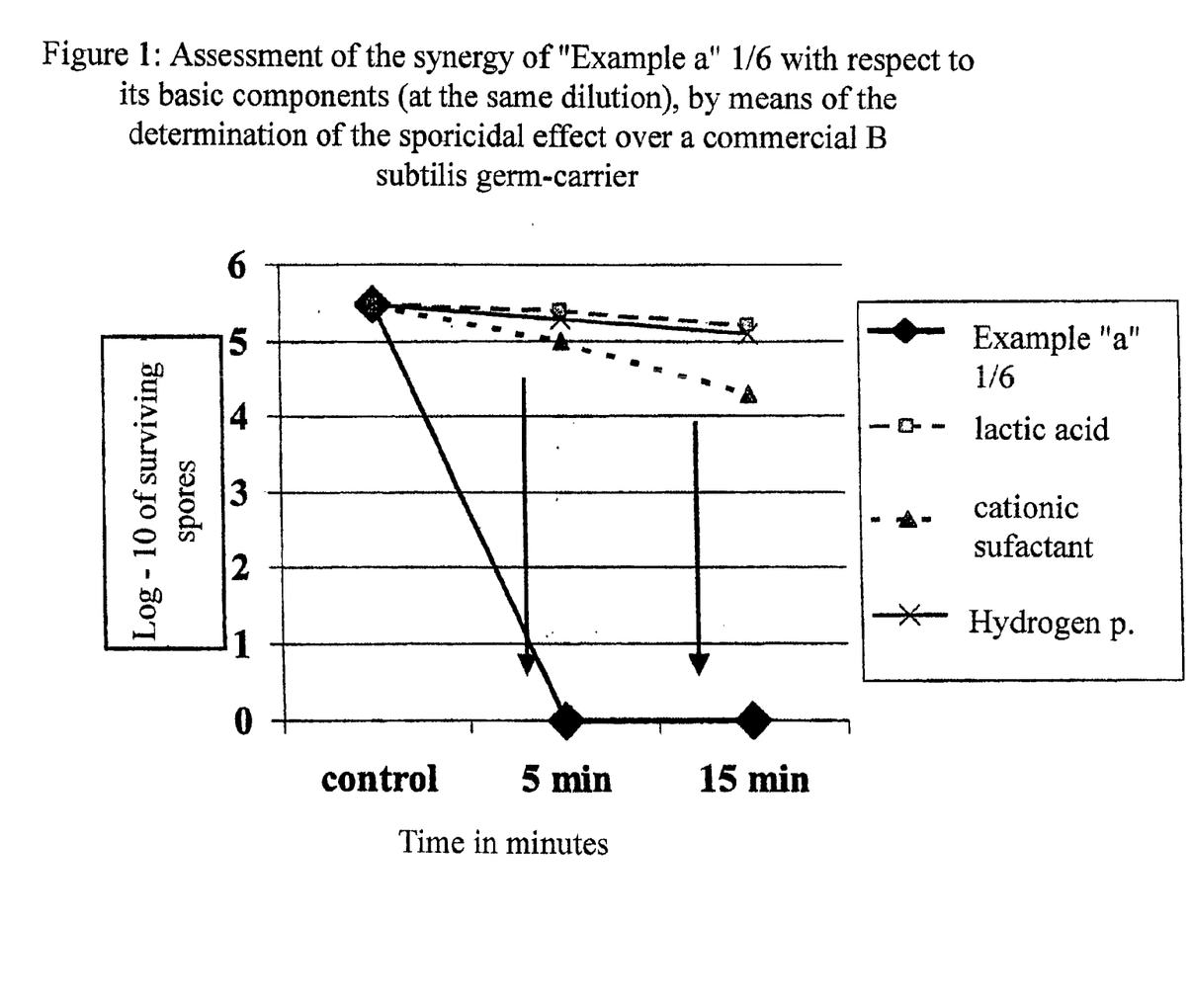
Figure 1: Assessment of the synergy of "Example a" 1/6 with respect to its basic components (at the same dilution), by means of the determination of the sporicidal effect over a commercial B subtilis germ-carrier
Figure 2:
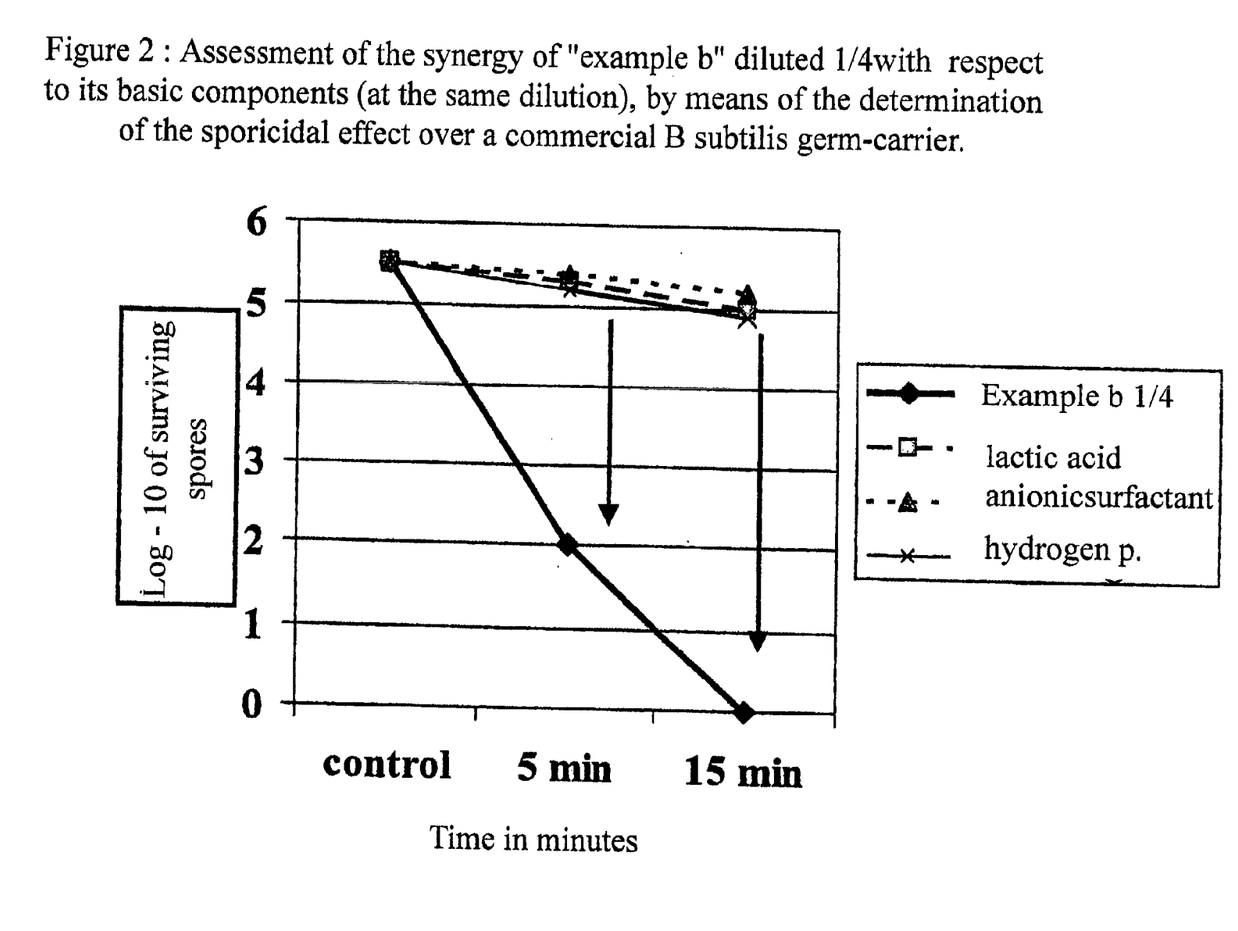
Figure 2: Assessment of the synergy of "example b" diluted 1/4 with respect to its basic components (at the same dilution), by means of the determination of the sporicidal effect over a commercial B subtilis germ-carrier.

The disinfecting composition of the invention has a much greater synergic effect than that expected from the simple addition of the products present in it:

In this sense, it was surprising to verify that the combination of hydrogen peroxide with lactic acid and surfactants (whether anionic or cationic), plus excipients, has a synergic effect, as may be seen in FIGS. 1 and 2 (said synergy being marked by the arrows descending from the best of the basic components to the mixture) as well as in examples 1–9 which show that said combinations increase its microbicidal capacity and decreases the oxidising effect of hydrogen peroxide, which does not alter the instruments, hence being suitable for disinfecting any material, including hospital material, preventing the problems described in disinfecting with hydrogen peroxide in the equipment and persons using it for the disinfecting of endoscopes, haemodialisers, etc.

On the other hand, the antiseptic variant of this invention is also based on a synergic effect, as will be shown afterwards, due to the combination of chlorhexidine, certain quaternary ammonium salts and iodine.

Besides, if this mixture of halogens with chlorhexidine and quaternary ammonium salts, is added at a ratio of 10–30% to 60° ethyl or isopropyl alcohol (this alcohol completing the remaining solution by 90–70%), a fast action antiseptic may be obtained which effectively acts over healthy skin, eliminating the acquired flora and reducing the autochthonous one, as will be shown later.

The tests described below show that the disinfecting composition of the invention is very useful for disinfecting hospital or non-hospital material, even if complex, with rough surfaces, etc. where other disinfecting products may fail. The variants with antiseptic action are harmless for the skin, such that they may constitute good antiseptic products, improving the effectiveness and persistence of reference antiseptic action, 10% povidone-iodine.

The disinfecting and antiseptic composition of the invention is obtained by mixing its basic compounds in suitable amounts, stirring until total homogenisation, although in certain formulas, some of the basic compounds may only bind to the rest at the time of activation, which is usually the same time as dilution in water.

Structured in two parts, according to the main indication as antiseptics or disinfectants, the following examples are specific and illustrative embodiments of the composition of this invention and must not be considered as limiting its scope.

Part 1: Disinfectants (Main Activity)

EXAMPLE 1

Preparation of a Disinfecting Composition

A disinfecting composition was prepared including:

| | |
|---|---|
| hydrogen peroxide: | 16% |
| lactic acid. | 24% |
| alkaline metal lauryl sulphate | 20% |
| halogen salts (Br, I): | 0.4% |

The composition was obtained by mixing the appropriate amounts of each component and stirring until complete homogenisation.

The efficacy was proved by carrying out the following tests:

Study of the bactericidal effect of the undiluted composition as well as when diluted to ½ and ¼.

Determination of the conservation of the concentrated and diluted solution activity during 2 weeks.

Instrument Deterioration Test.

For the determination of these three effects, the methods described by Herruzo et al in 1999 were used (Rev Stomatol Chir maxillofac 1999; 100: 299–305), which may be resumed as follows:

a) Bactericidal effect on instruments difficult to disinfect: No. 25 endodontic files.

These files are contaminated in a micro-organism for 30 minutes and after drying for 15 minutes in an oblique position, they are introduced in the disinfectant for 5, 10, 15, 20, etc. minutes. Afterwards, they are removed and submerged in a tube with glass beads and a disinfectant inhibitor (broth plus 6% Tween 80, plus 0.5% sodium bisulphite and 0.5% sodium thiosulphate). The tubes are then stirred for 1 minute to detach the surviving micro-organisms, and samples are cultured over the entire surface of agar plates with the culture medium suitable for the tested micro-organism (Müeller-Hinton or Saboureaud-dextrose for yeasts or HIB for mycobacteria, etc.). The control is similar in the whole test (disinfectant), except that the contaminated endodontic file is introduced in sterile distilled water and the culture is performed in progressive dilutions to count the cfu (colony forming units).

b) After preparation, the solution is left at room temperature for 7–14 days and the trial is repeated, as just described, but only with micro-organisms resistant to disinfecting: *P. Aeruginosa* and *Mycobacterium fortuitum*.

c) The effect on the metallic material is obtained by submerging a scalpel, after being removed from its sheath, in the different dilutions of the disinfectant composition. It is left at room temperature and the blackening or deterioration is observed during one week (equivalent to more than 2000 rinses of 10 minutes). It is recorded if there was any deterioration or not and the time at which it occurred. This test may be complicated if the first step consists in submerging the scalpel in blood (coming from a blood bank), since some of the disinfectants help to detach this organic material while others, fix it and collaborate in the deterioration of the scalpel.

The results are the following on 5 strains of each one of the species indicated: *S. aureus, S. epidermidis, E. faecalis, E. coli, K. pneumoniae, E. cloacae, P. mirabilis, Acinetobacter baumanii, P. aeruginosa* and *C. albicans*. Also, two *Mycobacterium fortuitum* strains were used (collections ATCC 609 and ATCC 6841). The tests were repeated five times with each one of the collection strains.

The time was ten minutes contact with the disinfectant for all cases.

| Micro-organism | control cfu (mean) | test cfu (mean) (dilution 1/1) |
|---|---|---|
| S. aureus | 135000 | 0 |
| S. epidermidis | 67000 | 0 |
| E. faecalis | 25000 | 0 |
| E. coli | 236000 | 0 |
| K. pneumoniae | 35000 | 0 |

-continued

| Micro-organism | control cfu (mean) | test cfu (mean) (dilution 1/1) |
|---|---|---|
| E. cloacae | 41000 | 0 |
| P. mirabilis | 39000 | 0 |
| A. baumanii | 64000 | 0 |
| P. aeruginosa | 190000 | 0 |
| C. albicans | 12500 | 0 |
| M. fortuitum 609 | 78000 | 0 |
| M. fortuitum 6841 | 56000 | 0 |

Similar results were obtained in ½ and ¼ dilutions.

The repetition of the trial with *P. aeruginosa* and *M. fortuitum* 609 at 7 and 14 days, produced identical results, involving a stability of at least 14 days without use.

The deterioration of metallic instruments as labile as the scalpel blade, impregnated or not with organic material, was nil, indicating good cleaning capacity and harmlessness before this model.

On studying 2% glutaraldehyde for 20 minutes in parallel (which is the reference disinfectant, although toxic and for this reason is replaced by formulas not having this negative feature), similar results were obtained in all strains except in Mycobacterium, against which, it did not completely destroyed the inoculum (not even in the time of use, 20 minutes, that is, twice than used for the disinfectant of the invention). Moreover, when the scalpel model is studied with this alkylising agent, the influence of the need of a good rinse may be observed, since if the scalpel did not have any organic material, several days would be required for deterioration of the model, but if it were impregnated with blood, it would deteriorate in only a few hours.

EXAMPLE 2

Preparation of a Disinfecting Composition

A disinfecting composition containing the following was prepared:

| | |
|---|---|
| hydrogen peroxide | 11% |
| lactic acid | 16% |
| didecyl-methyl-polyoxy-ethyl-ammonium propionate: | 32% |
| silver halides | 0.01% |

The composition was prepared by mixing suitable amounts of each components and stirring until complete homogenisation.

The effectiveness was shown by performing the following tests:

Study of the bactericidal effect of the undiluted composition, as well as that diluted to ½, ¼, ⅙ and ⅛.

Determination of the preservation of the concentrated and diluted solution activity, during 2 weeks.

Instrumental Deterioration Test.

The methodology is similar to that described in the previous example, except for the fact that the studies were performed in a time of 5 minutes instead of 10 and a greater dilution was reached, ⅛.

The results were similar to the previous ones, 0 survivors in all cases, besides remaining active for at least 2 weeks and the scalpel not deteriorating, with or without blood.

In this case, another more demanding test was used, since the sporicidal effect was assessed. It is similar to the bactericidal effect, but instead of contaminated instruments, a commercial, cellulose germ holder was used, impregnated in spores. In fact, this is the biological control used in sterilisation by ethylene oxide: spores of B subtilis, at a concentration guaranteed by the manufacturer (3M) and which exceed a million spores per germ holder. The rest was similar to that described in the endodontic file method.

The results were excellent, since 5 decimal logarithms were destroyed in only 5 minutes in the 1/1 to 1/8 solutions. When lower dilutions (only with this germ) were also used, namely 1/20 and 1/50, during 10 minutes, the effect was lower, 2.6 log 10 and 1.9 log 10 of reduction, respectively, but it was still sufficiently useful since if we compare it with the reference disinfectant, 2% glutaraldehyde, in this time (10 minutes) it only reduced the inoculum by 1.5 log 10.

In the successive examples, the number of micro-organisms used was reduced, since only 3 strains of the following species (isolated from ICU patients) were used: *P. aeruginosa, S. aureus, E. coli, E. faecalis*, together with the *M. fortuitum* strains of the ATCC 609 collection and *B. subtilis* spores.

EXAMPLE 3

A disinfectant composition containing the following was prepared:

| | |
|---|---|
| hydrogen peroxide | 9% |
| lactic acid | 4.9% |
| chlorhexidine | 18% |
| silver halides | 0.1% |

The composition was obtained by mixing the suitable amounts of each compound and stirring until complete homogenisation.

The effectiveness was shown by performing the following tests:

Study of the bactericidal effect of the undiluted composition, as well as dilutions at 1/2, 1/4, 1/6 and 1/8.

Determination of the preservation of the concentrated and diluted solution activity, during 2 weeks.

Instrumental Deterioration Test.

The methodology is similar to that described in the previous example 2, except that the studies were performed until a lesser dilution, 1/6, in 5 minutes and until 1/8, in 10 minutes.

The results were similar to the previous ones, 0 survivors in all cases (plus 5 log reduction, including the spores), remaining active at least 2 weeks and not deteriorating the scalpel, with or without blood.

EXAMPLE 4

A disinfecting composition was prepared containing:

| | |
|---|---|
| hydrogen peroxide: | 21% |
| lactic acid | 18% |
| didecyl-methyl-polyoxy-ethyl-ammonium propionate | 6% |
| silver halides: | 0.001% |

The composition was obtained by mixing suitable amounts of each compound and stirring until complete homogenisation.

The effectiveness was shown by performing the following tests:

Study of the microbicidal effect of the undiluted composition, as well as 1/2, 1/4 and 1/6 dilutions.

Determination of the preservation of the concentrated and diluted solution activity during 2 weeks.

Instrument Deterioration Test.

The methodology and results were similar to those of the previous example, but the 1/8 dilution was not used.

EXAMPLE 5

A disinfecting composition was prepared, containing:

| | |
|---|---|
| hydrogen peroxide: | 11% |
| lactic acid: | 16% |
| didecyl-methyl-polyoxy-ethyl-ammonium propionate | 24% |
| chlorhexidine | 12% |
| silver halides | 0.05% |

The composition was obtained by mixing suitable amounts of each compound and stirring until complete homogenisation.

The effectiveness was shown by performing the following tests:

Study of the bactericidal effect of the undiluted composition, as well as 1/2, 1/4, 1/6 and 1/8 dilutions.

Determination of the preservation of the concentrated and diluted solution activity, during 2 weeks.

Instrument Deterioration Test.

The methodology and results were similar to those of Example 3.

Another formula (EXAMPLE 6) with similar results in its 1/1 to 1/6 dilutions in only 5 minutes and 10 minutes in dilution 1/8, was the following (undiluted formulation):

| | |
|---|---|
| hydrogen peroxide: | 6.1% |
| lactic acid: | 4.8% |
| didecyl-methyl-polyoxy-ethyl-ammonium propionate | 50% |
| chlorhexidine: | 6% |
| silver halides: | 0.01% |

OTHER EXAMPLES 7.1 With Other Anionic Surfactants:

7.1.1.:

| | |
|---|---|
| Hydrogen peroxide: | 0.2% |
| Lactic acid: | 0.1% |
| Dodecyl sulphate salts. | 0.2% |
| Ethyl or isopropyl alcohol (60°): | until completing 100% |

Methodology: it was studied by a contaminated surface model, using a sterile cotton cloth germ-carrier (Herruzo et al, Rev. Esp. Microbil Clin, 1990; 5:197–202), which was then contaminated with a micro-organism. Then, it was introduced in the disinfectant for 5 minutes and removed to submerge it in 5 ml disinfectant inhibitor with glass beads. The rest was similar to that described in Example 1 with the endodontic file germ-carrier.

Results: 4 micro-organisms were used, which are normally found on hospital surfaces: *P. aeruginosa, S. aureus, E. cloacae,* and *C. albicans,* all of them isolated from clinical samples. The results were excellent in only 5 minutes direct application.

| Micro-organism | Control (before) | Disinfectant (after application) |
|---|---|---|
| *P. aeruginosa* | 2500 | 0 |
| *S. aureus* | 6900 | 0 |
| *E. cloacae* | 3600 | 0 |
| *C. albicans* | 4200 | 0 |

7.1.2.: The same formula as used in Example 1, but replacing lauryl sulphate by dodecyl sulphate, which in the undiluted formulation is:

| | |
|---|---|
| hydrogen peroxide: | 16% |
| lactic acid: | 24% |
| dodecyl sulphate salts: | 12% |
| halogen salts (Br, I): | 1% |

It was used at ⅓, ½ and ¼ dilutions with *Mycobacterium fortuitum* 609 and *B. subtilis* spores (with the bactericidal and sporicidal methodology described in Examples 1 and 2):

Both the concentrated solution and ½ and ¼ dilutions destroyed the inoculii (>5 log 10) in 10 minutes.

7.1.3: The same formula as used in Example 1, but replacing lauryl sulphate by alkylsuccinic, which in the undiluted formulation is:

| | |
|---|---|
| hydrogen peroxide: | 16% |
| lactic acid: | 24% |
| alkyl succinic salts: | 12% |
| halogen salts (Br, I): | 2% |

⅓, ½ and ¼ dilutions were also used with *Mycobacterium fortuitum* and *B. subtilis* spores (with the bactericidal and sporicidal methodology described in Examples 1 and 2).

Both the concentrated solution and ½ and ¼ dilutions destroyed the inoculii (>5 log 10) in 10 minutes.

7.2. Cationic Surfactants:

7.2.1.: A formula was made which in a concentrated solution contained:

| | |
|---|---|
| hydrogen peroxide: | 22.5% |
| lactic acid: | 2% |
| chlorhexidine: | 0.3% |
| silver halides | 0.0004% |

It was also used at ⅓, ½ and ¼ dilutions with *Mycobacterium fortuitum* 609 and *B. subtilis* spores (with the bactericidal and sporicidal methodology described in Examples 1 and 2).

The ⅓ and ½ concentrated solutions destroyed the inoculii (>5 log 10) in 10 minutes and the ¼ dilution, destroyed more than 3 log 10 in the same time.

7.2.2.: A formula was made, which in a concentrated solution contained:

| | |
|---|---|
| hydrogen peroxide: | 6.1% |
| lactic acid: | 4.0% |
| ammonium chlorides: | 50% |
| silver halides: | 0.001% |

⅓, ½, ¼ and ⅛ dilutions were used with *Mycobacterium fortuitum* 609 and *B. subtilis* spores (with the bactericidal and sporicidal methodology described in Examples 1 and 2):

The ⅓ and ½ concentrated solutions destroyed the inoculii (>5 log 10) in 5 minutes and the ¼ and ⅛ dilutions, reached the same effectiveness in 10 minutes.

7.2.3. A formula was made, which in a concentrated solution contained:

| | |
|---|---|
| hydrogen peroxide: | 6.1% |
| lactic acid: | 4.0% |
| ammonium propyl amide salts: | 50% |
| silver halides: | 0.001% |

⅓, ½, ¼ and ⅛ dilutions were used with *Mycobacterium fortuitum* 609 and *B. subtilis* spores (with the bactericidal and sporicidal methodology described in Examples 1 and 2):

The ⅓ and ½ concentrated solutions destroyed the inoculii (>5 log 10) in 5 minutes and the ¼ and ⅛ dilutions reached the same effectiveness in 10 minutes.

In the examples 7.2.2 and 7.2.3, as well as in those described with numbers 2, 3, 4, 5 and 6, the silver salts may be replaced (or added) by iodine, bromine salts or metallic iodine, at a 0.5–5% concentration in the concentrated formulas, with similar results.

On the other hand, any of the previous formulas may be used with enzymes, to obtain enzymatic products, for which we will give some examples, not limiting the possibilities of these formulas:

EXAMPLE 8

The concentrated solution contains:

| | |
|---|---|
| hydrogen peroxide: | 6.1% |
| lactic acid: | 4.5% |
| didecyl-methyl-polyoxy-ethyl-ammonium propionate: | 20% |
| enzymes: trypsin, lipase, amylase: 1–10 ml of each one per ml of final concentrated solution. | |

It is diluted 100 times and used as a preliminary rinse prior to instrument disinfecting, during 15 minutes. Its effect is checked with the same endodontic file test described previously, against *P. aeruginosa, E. cloacae, Mycobacterium fortuitum* 609 and commercial *B. subtilis* spores.

The results are a reduction of more than 2 log 10 of all these micro-organisms, while other commercial enzymatic solutions, in which a similar dilution is recommended, only reached 0.1–0.9 log 10.

EXAMPLE 9

The concentrated solution contains:

| | |
|---|---|
| hydrogen peroxide: | 6.1% |
| lactic acid: | 4.5% |
| lauryl sulphate salts (or dodecyl sulphate): | 10% |
| enzymes: trypsin, lipase, amylase: 1–10 ml of each one per ml of final concentrated solution. | |

The dilutions and results are similar to those of the previous example.

Part 2: Antiseptics (Prevalent Activity)

Finally, as mentioned in the first page, the composition of this invention may also be used for antisepsis.

The base of this formulation is in the synergy found between a non-chlorinated quaternary ammonium and chlorhexidine and of the latter with halogens (iodine and derivatives). This is shown by means of its MIC (minimum inhibiting concentration).

A MIC is obtained in a solid medium against *S. aureus* and *P. aeruginosa*.

The results were the following:

Didecyl-metyl-polyoxy-ethyl-ammonium propionate 50% (=Pro)

Chlorhexidine 20% (=clo)

Iodine 1% (=I)

| Product | *S. aureus* | *P. aeruginosa* |
|---|---|---|
| Pro | 1/20480 | 1/160 |
| Clo | 1/20480 | 1/2560 |
| Pro + Clo | 1/40960 | 1/10240 |
| I | 1/20 | <1/20 |
| Pro + I | >1/40960 | 1/160 |
| Clo + I | 1/40960 | 1/5120 |

As may be observed, the MIC increase in the combinations of products indicates synergy between them, since the mixture is diluted to the half with respect to the individual products.

To determine the bactericidal activity, two classes of tests were used:

a) "in vitro", following that described by Herruzo et al 1991 (Burns, 1991; 18:35–38).

b) "in vivo", with the methodology mentioned by Herruzo et al, 2000 (Journal of Surgical Research 2000; 94: 6–12) and a modification of this to artificially contaminate the hands. Basically, the tests are as follows:

a) In vitro: 0.5 mm diameter lyophilised pig skin (commercial) circles are cut and sterilised. Afterwards, they are submerged in a micro-organism for 1 hour and left to dry in an inclined position during 15 minutes. Then, they are introduced in the antiseptic during 1 or 3 minutes and finally, the microbicidal is inactivated with the inactivator used in the previous test (6% Tween 80, plus 0.5% sodium bisulphite, plus 0.5% sodium thiosulphate). The rest is like that described in the test with the endodontic files.

b) In vivo without artificial contamination of the hands: The 4 index-little finger of the non-predominating hand are submerged in 10 ml of the previously mentioned disinfecting inhibitor and shaken inside the inhibitor liquid for 1 minute. Then, cultured in 0.1 ml Mueller-Hinton and extend over the plate. This is the initial natural contamination control. Then, the hand is rinsed with water to eliminate the inhibitor and then rinse with the product to be tested for 3 minutes, rubbing it between both hands (without a surgical brush). Afterwards, the fingers of the predominating hand, etc. are submerged to compare the number of cfu of each one.

c) In vivo with artificial contamination of the hands: 2 ml of a 24 hour culture of *P. aeruginosa* are applied over them, letting them to dry for 5 minutes. Afterwards, continue as in the previous experiment, but in the control dilutions are also made before sowing the plate, to be able to make an adequate count of the number of cfu (generally 1000–10000).

The formulas used were (without this being limiting):

EXAMPLE 10

| | |
|---|---|
| Didecyl-methyl-polyoxy-ethyl-ammonium propionate: | 5–20% |
| chlorhexidine | 1–5% |
| iodine or iodinated salts: | 0.1–5% |
| emollients: | 1–2% |
| water, until completing: | 100% |

EXAMPLE 11

| | |
|---|---|
| Didecyl-methyl-polyoxy-ethyl-ammonium propionate: | 5–20% |
| chlorhexidine: | 1–5% |
| iodine or iodinated salts: | 0.1–5% |
| emollients: | 1–2% |
| alcohol 60°, until completing 100% | |

EXAMPLE 12
(to be used on persons with allergy to iodine):

| | |
|---|---|
| Didecyl-methyl-polyoxy-ethyl-ammonium propionate: | 5–20% |
| chlorhexidine: | 7.5% |
| emollients: | 1–2% |
| water, until completing 100% | |

EXAMPLE 13
(to be used by persons with allergy to iodine):

| | |
|---|---|
| Didecyl-methyl-polyoxy-ethyl-ammonium propionate: | 5–20% |
| chlorhexidine: | 7.5% |
| emollients: | 1–2% |
| 60° alcohol, until completing 100% | |

The results with respect to 10% iodinated povidone (PVPI), the antiseptic most used in surgical rinsing, were:

a) In vitro test:

| Micro-organism | Control Mean cfu | Mean cfu |
|---|---|---|
| | | Example, 1 min |
| *P. aeruginosa* | 1400 | No. 10 = 2 |
| | | No. 11 = 0 |
| | | No. 12 = 0 |

| | | |
|---|---|---|
| | | No. 13 = 0 |
| | | PVPI = 75 |
| S. aureus | 4600 | No. 10 = 0 |
| | | No. 11 = 0 |
| | | No. 12 = 0 |
| | | No. 13 = 0 |
| | | PVPI = 25 |
| | | Example, 3 min |
| P. aeruginosa | 1400 | No. 10 = 0 |
| | | No. 11 = 0 |
| | | No. 12 = 0 |
| | | No. 13 = 0 |
| | | PVPI = 0 |
| S. aureus | 4600 | No. 10 = 0 |
| | | No. 11 = 0 |
| | | No. 12 = 0 |
| | | No. 13 = 0 |
| | | PVPI = 12 | b) In vivo studies (healthy volunteers n = 15)

| | | |
|---|---|---|
| b.1) Normal flora | initial | after rinsing |
| | (log 10 cfu) | (log 10 cfu) |
| | (mean E ± S) | (mean E ± S) |
| | 4.24 ± 0.3 | Example 10 0 |
| | | Example 11 <0 |
| | | Example 12 <0 |
| | | Example 13 <0 |
| | | PVPI 0.48 ± 0.3 |
| b.2) Acquired flora | initial | after rinsing |
| (P. aeruginosa) | (log 10 cfu) | (log 10 cfu) |
| | (mean E ± S) | (mean E ± S) |
| | 5.26 ± 0.4 | Example 10 0.3 ± 0.3 |
| | | Example 11 <0 |
| | | Example 12 0.1 ± 0.1 |
| | | Example 13 <0 |
| | | PVPI 1.98 ± 0.3 |

As may be observed, it is more effective than the reference antiseptic, although the difference is appreciated even more if we study the persistence of the antiseptic effect for two hours under a surgical glove
(where there is sweating and recontamination of the hand surfaces as from the micro-organisms housed in the bottom of the sebaceous glands, pillose follicles, etc.). For this purpose, a test is performed, similar to that described in the "in vivo" methods with natural flora, but samples are taken of the natural contamination of both hands, after rinsing and taking samples from the predominating hand. Then, the hands are dried (with the help of a collaborator) with a sterile towel and surgical gloves worn. After two hours, the volunteer removes the glove and a sample taken from the non-predominating hand, in the same way as in the previous trial. Therefore, we have three results: before, immediately after and at 2 hours.

The results at 2 hours were excellent (no micro-organisms surviving: log 10<0) in examples 11 and 13 (that is, in those with alcoholic solution) and in 10 and 12, the flora obtained increased log 10 with respect to that obtained after rinsing, but still more than 3 log 10 below the initial result. However, PVPI, the reference antiseptic, hardly has residual power, since the log 10 cfu obtained after removing the glove at 2 hours is 2–3 units greater than that after rinsing and even, sometimes, exceeds that obtained before rinsing, indicating the risk of contamination of the surgical environment in the case of puncturing the glove after this surgical intervention time.

Not significantly different effects have been obtained by replacing this quaternary ammonium by other non-chlorinated quaternary ammonium salts (data not shown).

What is claimed is:

1. A composition comprising the following components: hydrogen peroxide in an amount of 6.1–22.5% by weight, lactic acid in an amount of 0.1–24% by weight, and a cationic surfactant selected from the group consisting of a biguanidine, a quaternary ammonium chloride and didecyl-methyl-polyoxy-ethyl-ammonium-propionate, said components being present in respective amounts effective to provide the composition with an anti-microbial activity that is greater than an anti-microbial activity of each of the components singly, the composition further comprising an additive that further enhances the anti-microbial activity of the composition.

2. The composition according to claim 1, wherein the surfactant is a quaternary ammonium chloride.

3. The composition according to claim 1, wherein the surfactant is biguanidine.

4. The composition according to claim 1, wherein the surfactant is didecyl-methyl-polyoxy-ethyl-ammonium propionate present in the composition in an amount of 0.2–50% by weight.

5. The composition according to claim 4, wherein the additive is selected from the group consisting of trypsin, lipase, amylase and a combination thereof.

6. The composition according to claim 4, wherein the additive is a silver halide.

7. A disinfecting and antiseptic composition, comprising hydrogen peroxide in an amount of 6.1–22.5% by weight, lactic acid in an amount of 0.1–24% by weight, and at least one cationic surfactant selected from the group consisting of quaternary ammonium salt and a biguanidine.

8. A composition according to claim 7, wherein the biguanidine is chlorhexidine.

9. A composition according to claim 7 wherein the cationic surfactant is a non-chlorinated quaternary ammonium salt.

10. A composition according to claim 7, wherein the non-chlorinated quaternary ammonium salt is didecyl-methyl-polyoxy-ethyl-ammonium propionate.

11. A composition according to claim 7, further comprising at least one salt selected from the group consisting of a halogen salt and a heavy metal salt.

12. A composition according to claim 11, wherein the halogen salt is a bromide or an iodide.

13. A composition according to claim 11, wherein the salt is a halogen salt which is silver or cerium halide.

14. A composition according to claim 7, wherein the surfactant is a biguanidine which is a present in the composition in an amount of 0.1% to 18% by weight.

15. A composition according to claim 7, wherein the surfactant is a quaternary ammonium chloride which is present in the composition in an amount of 0.2% to 50% by weight.

16. A composition according to claim 9, wherein the surfactant is a non-chlorinated quaternary ammonium salt which is present in the composition in an amount of 0.2% to 50% by weight.

17. A composition according to claim 11, wherein the at least one salt is a halogens alt which is present in the composition in an amount of 0.00 1% to 5% by weight.

18. A composition according to claim 11, wherein the at least one salt is a metal salt which is present in the composition in an amount of 0.0002% to 2% by weight.

19. A composition according to claim 7, further comprising an enzyme.

20. A composition according to claim 19, wherein the enzyme is selected from the group consisting of trypsin, amylase, lipase and a combination thereof.

21. A composition according to claim 20, wherein the enzyme is present in the composition in an amount of 1–10 units/ml.

22. A composition according to claim 21, further comprising at least one excipient.

23. A composition according to claim 1 comprising the following compounds in the following percentages by weight:

| | |
|---|---|
| hydrogen peroxide: | 6.1–22.5% |
| lactic acid: | 0.1–24% |
| chlorhexidine: | 5.1–18% |
| heavy metal salt | 0.0002–0.1% |

24. A composition according to claim 1, comprising the following components in the following percentages by weight:

| | |
|---|---|
| hydrogen peroxide: | 0.2–2.9% or 6.1–22.5% |
| lactic acid: | 0.1–24% |
| dodecyl-methyl-polyoxy-ethyl-ammonium propionate: | 0.2–12% |
| a silver halide: | 0.1–5% |
| water and excipient | balance to 100% |

25. A composition according to claim 1, comprising the following components in the following percentages by weight:

| | |
|---|---|
| hydrogen peroxide: | 0.2–2.9% or |
| lactic acid: | 0.1–24% |
| didecyl-methyl-polyoxy-ethyl-ammonium propionate: | 0.2–50% |
| chlorhexidine: | |
| a silver halide: | 0.00001–0.1% |
| water and excipient | balance to 100% |

26. A composition according to claim 23, further comprising an enzyme selected from the group consisting of trypsin, amylase, lipase and a combination thereof.

27. A composition according to claim 24, further comprising an enzyme selected from the group consisting of trypsin, amylase, lipase and a combination thereof.

28. A composition according to claim 25, further comprising an enzyme selected from the group consisting of trypsin, amylase, lipase and a combination thereof.

* * * * *